United States Patent [19]
Devon et al.

[11] Patent Number: 5,177,019
[45] Date of Patent: Jan. 5, 1993

[54] METHOD OF QUANTITATIVE ANALYSIS OF ORGANOPHOSPHORUS COMPOUNDS

[75] Inventors: Thomas J. Devon; Jerry C. Dobbs, both of Longview, Tex.

[73] Assignee: Eastman Kodak Company, Rochester, N.Y.

[21] Appl. No.: 702,484

[22] Filed: May 20, 1991

[51] Int. Cl.$^5$ .............................................. G01N 30/14
[52] U.S. Cl. .................................. 436/104; 436/103; 436/161; 436/174; 436/176
[58] Field of Search ................... 436/73, 84, 103, 104, 436/161, 174, 176; 568/454

[56] References Cited

U.S. PATENT DOCUMENTS

| | | | |
|---|---|---|---|
| 3,624,095 | 11/1971 | Poirier et al. | 436/104 |
| 3,910,763 | 10/1975 | Poziomek et al. | 436/104 |
| 4,507,503 | 3/1985 | Frey et al. | 568/17 |
| 4,599,206 | 7/1986 | Billig et al. | 568/454 |
| 4,801,754 | 1/1989 | Bach et al. | 568/454 |

FOREIGN PATENT DOCUMENTS 0233428  2/1989  U.S.S.R. .

OTHER PUBLICATIONS

Dietmar, Thiele: "Recovery of complexed heavy metal ions from diluted aqueous Cyanide-Containing Solutions"; Chem. Abs. vol. 104, No. 10, Mar. 1986, 72426g.

Blaha et al., "Multiresidue method for quantitave determination of organophosphorus pesticides in food"; Chem. Abs. vol. 104, No. 5, Feb. 1986, 33159g.

Cervinka et al.; "Rhodium recovery from Organo-Complexes"; Chem. Abs. vol. 105, No. 2, Jul. 1986, 9842v.

Primary Examiner—James C. Housel
Assistant Examiner—Ramon Torres
Attorney, Agent, or Firm—J. Frederick Thomsen; William P. Heath, Jr.

[57] ABSTRACT

A novel method quantitatively analyzes certain organophosphorus compounds present in mixtures of the organophosphorus compounds, a Group VIII metal and an inert solvent using gas chromatography techniques. The method involves the conversion of a catalytically-active form of the Group VIII metal to a cyano complex prior to gas chromatography analysis. Compositions are also described which are useful in the gas chromatography analysis.

8 Claims, No Drawings

METHOD OF QUANTITATIVE ANALYSIS OF ORGANOPHOSPHORUS COMPOUNDS

This invention pertains to a novel method for the quantitative analysis of certain organophosphorus compounds present in mixtures of the organophosphorus compounds, a Group VIII metal and an inert solvent using gas chromatography techniques. More specifically, this invention pertains to the accurate measurement of organophosphorus compounds in the presence of a Group VIII metal wherein the Group VIII metal is converted to a cyano complex prior to gas chromatography analysis. This invention also pertains to compositions useful in the gas chromatography analysis.

Several known chemical processes employ catalyst systems comprising a Group VIII transition metal in combination organophosphorus compounds which function as stabilizing ligands for the Group VIII metal. Examples of such catalyst systems include dimerization catalysts such as cobalt in combination with 1,2-bis(diphenylphosphino)ethane, useful for the conversion of ethylene and butadiene into cis-1,4-hexandiene as described by Olive and Olive, J. Organometal. Chem. 35, 381 (1972); cyclodimerization and cyclotrimerization catalysts for butadiene using nickel in combination with triphenylphosphine and tri-n-butylphosphine modified nickel as described by Khan and Martell, Homogeneous Catalysis by Metal Complexes, Vol III pp. 161, 162 (1974), Academic Press; palladium in combination with trialkyl and triaryl-phosphine modified palladium catalysts useful in the production of α-ketoesters from arylhalides as described by Tanaka, J. Molecular Cat., 32, 115–118 (1985).

The hydroformylation reaction is of great commercial utility in the preparation of oxygenated compounds such as aldehydes and alcohols by the transition metal catalyzed reaction of olefins with carbon monoxide and hydrogen. The original high pressure catalyst technology based on cobalt carbonyl is rapidly being replaced with low pressure rhodium catalyst systems that use organophosphorus ligand modifiers. Such a catalyst system using rhodium in combination with triaryl-phosphines such as triphenyl phosphine, described in U.S. Pat. No. 3,527,809, was the first low pressure hydroformylation process to be commercialized. Hydroformylation processes employing of catalyst systems comprising combinations of rhodium and diphenylalkylphosphines are described in U.S. Pat. No. 4,260,828 and U.S. Pat. No. 4,593,141. U.S. Pat. Nos. 4,137,240 and 4,599,206 disclose hydroformylation processes wherein the catalyst system comprises combinations of rhodium with organophosphites such as triphenylphosphite or cyclic organophosphite ligands.

The hydroformylation literature also includes references to the use of catalyst systems comprising rhodium and bis-phosphine compounds such as 1,1'-bis (diphenylphosphino)ferrocene (U.S. Pat. No. 4,138,420 and U.S. Pat. No. 4,152,344); trans-1,2-bis(diphenylphosphinomethyl)cycloalkanes) in combination with monodentate triorganophosphine compounds (U.S. Pat. No. 4,169,861); α,β-bis(diphenylphosphino)-2-ethyltoluene (U.S. Pat. No. 4,774,362) and 2,2'-bis(diphenylphosphinomethyl)-1,1'-biphenyl (U.S. Pat. No. 4,694,109) which is particularly useful for the preparation of aldehyde products with a high selectivity to linearity.

During the operation of the hydroformylation processes described above, the original organophosphorus component, including both mono and bis-phosphine compounds, of the catalyst systems is transformed into other, less effective compounds. For example, in processes utilizing rhodium and triphenylphosphine catalyst systems in the hydroformylation of propylene, some of the triphenylphosphine is converted into diphenylpropylphosphine. The detrimental effect of the diphenylpropylphosphine on the overall performance of the catalyst has resulted in the development of processes for its removal. See, for example, the processes disclosed in U.S. Pat. No. 4,151,209 and U.S. Pat. No. 4,605,780. Another transformation/decomposition reaction which occurs is the conversion of organophosphine compounds to their corresponding phosphine oxides due to entry of small amounts of oxygen into the hydroformylation process with the feed materials. These phosphine oxides are not effective in stabilizing the rhodium component of the catalyst system. The quantitative analysis of the organophosphorus decomposition products is desirable to maintain the desired reaction rates and product mix of the hydroformylation processes.

In view of the transformation or decomposition of the organophosphorus component of the catalyst systems described herein, a general analytical method for the accurate, quantitative measurement of the concentrations of the original organophosphorus compound as well as decomposition products thereof is needed. In a general sense, other transition metal/triorganophosphine catalyst systems undergo Group VIII metal catalyzed organophosphorus decomposition under reaction conditions so that an accurate analysis of the organophosphorus compounds present in the catalyst solution would be valuable for operation control.

The quantitative analysis of air-sensitive organophosphorus compounds, particularly trisubstituted, mono and bis-phosphines, present in rhodium containing, hydroformylation, catalyst systems has always been a challenge. One method involves the potentiometric titration of the catalyst solutions containing relatively basic triorganophosphine compounds with a strong acid such as perchloric acid in an anhydrous solvent. Streuli, (Analytical Chemistry, 32, 985–987 (1960)) describes the use of this method in the determination of the basicity of triorganophosphine compounds. This method does not always produce accurate results since the perchloric acid reagent titrates other basic materials such as sodium or potassium carboxylate salts or alkyl amine impurities that may be present in the solutions analyzed. Furthermore, this method does not differentiate between different phosphine compounds such as triphenylphosphine and diphenylpropylphosphine mentioned above. Basic triorganophosphine ligands such as diphenylpropylphosphine titrate along with the triphenylphosphine yielding a single potentiometric end-point.

Catalyst systems comprising rhodium and 2,2'-bis(diphenylphosphinemethyl)-b 1,1'-biphenyl are especially effective in the hydroformylation of propylene to produce butyraldehyde product with a high selectivity to normal butyraldehyde. The analysis of bis-phosphine compounds such as 2,2'-bis(diphenylphosphinomethyl)1,1'-biphenyl poses additional analytical problems since the two phosphorus atoms of the bis-phosphine compounds are titrated by the acid. The phosphine oxide decomposition products pose no problem with respect to titration analysis of basic triorgano mono-phosphine compounds, such as triphenyl phosphine, so long as the corresponding phosphine oxides do not interfere with the titration method. A major error in the analysis of bisphosphine compounds, such as 2,2'-bis(diphenylphosphinomethyl)-1,1'-biphenyl, occurs when one of the two phosphorus atoms are converted to the oxide. The unoxidized phosphorus atom will titrate yielding an inaccurately high concentration of the bisphosphine compound. Since the monoxides of the bisphosphine compounds are detrimental to the performance of the rhodium/phosphine catalyst system, an accurate analytical method for determining the concentrations of the phosphines and their decomposition products is needed for optimum control of the hydroformylation processes.

Yet another problem associated with the titration method is that organophosphine compounds bound to rhodium are not titrated, producing an inaccurate, low phosphine analytical value. This problem is particularly critical when the mole ratio of phosphine:rhodium is low, as in the case of catalyst systems comprising rhodium and bis-phosphine compounds.

The characterization of organophosphorus compounds by means of phosphorus 31 nuclear magnetic resonance spectroscopy (31P NMR) has been disclosed by Verkade and Quin in "Phosphorus 31 NMR Spectroscopy in Stereochemical Analysis, Organic Compounds and Metal Complexes", VCH Publishers, Weinheim, FRG, (1987). The application of this technique for quantitative analysis is hindered by the relatively low sensitivity of the method at low phosphorus concentrations and variable sensitivities of the phosphorus nuclei of different compounds to the quantitative analysis because of the nuclear overhouser effect. Additionally, transition metals such as rhodium having nuclear spin also interfere with quantitative methods by causing chemical shift changes and peak splitting.

U.S. Pat. No. 4,507,503 discloses the analysis of mixtures of the very high boiling triphenylphosphine and its corresponding oxide by means of gas phase chromatography. The low vapor pressures of these compounds require the use of very hot injector port temperatures and column conditions in order to get a sharp peak to appear on the chromatograph. The chromatographic method allows the analysis of organophosphorus impurities that are inert to or interfere with the potentiometric titration.

The accuracy of gas chromatographic (GC) analyses of solutions of rhodium and bis-phosphine compounds is not entirely satisfactory due to the rhodium catalyzed decomposition of the bis-phosphine molecule in the injector port of the gas chromatograph. For example, when a mixture of rhodium and 2,2'-bis(diphenylphosphinomethyl)-1,1'-phenyl is injected into a gas chromatography instrument, three major unknown peaks are produced on the chromatograph. These three peaks have shorter retention times than the peak produced when pure 2,2'-bis(diphenylphosphinomethyl)-1,1'-phenyl is injected into the instrument. Attempts to suppress this decomposition process carried out using on-column injection techniques with cool starting temperatures failed due to poor peak quality and the observation of the peaks produced by the decomposition products.

We have discovered that the concentration of organo-phosphine compounds, including organo-phosphine oxides, present in mixtures of rhodium and such phosphine compounds may be determined with improved accuracy using conventional gas chromatographic (GC) instruments and procedures by converting the rhodium present in the mixture to a complex cyano-rhodium compound. Thus, one embodiment provided by the present invention pertains to a process for determining the concentration of organo-phosphine compounds in the presence of rhodium which comprises subjecting to GC analysis a solution comprising the organo-phosphine compounds, a complex cyano-rhodium compound and an inert, organic solvent. In accordance with well-known GC procedures, the solution analyzed typically will also contain an internal standard which permits the peaks of the chromatographs produced to be quantified. A second embodiment of our invention is represented by the solution used in the GC procedure.

The process of the present invention thus provides a means for determining the concentration of organo-phosphine compounds present in a solution containing a complex of an organo-phosphine compound and rhodium by the steps of:

(1) contacting the solution with a cyano reagent to convert the organo-phosphine:rhodium complex to a cyano-rhodium complex; and (2) subjecting the mixture obtained from step (1) to gas-liquid chromatography analysis.

Step (1) further comprises contacting the solution containing a complex of an organo-phosphine compound and rhodium with a second solution comprising a cyano reagent, a gas chromatographic internal standard and an inert solvent to convert the organo-phosphine:rhodium complex to a cyano-rhodium complex.

The material that is used in the analysis according to our invention is obtained from a hydroformylation production system wherein an olefin such as propylene is contacted with carbon monoxide and hydrogen in the presence of (1) a catalyst system comprising a rhodium and one or more organo-phosphine compounds and (2) an inert solvent such as 2-ethylhexanal, 2,2,4-trimethylpentanediol monoisobutyrate, toluene and other materials described in the literature as suitable hydroformylation process solvents. The sample of liquid material to be analyzed may be taken from the hydroformylation reactor or from a catalyst recycle stream, depending on mode in which the production system is operated. The catalytically active material contains rhodium in complex combination with carbon monoxide and organo-phosphine ligands. The analytical samples should be taken and handled subsequently in an oxygen-free environment to avoid air oxidation of the air-sensitive, organo-phosphine components of the catalyst system.

A portion of the sample is transferred to a small container, the weight of the amount transferred is determined and then a predetermined amount of a solution of a cyano reagent and, optionally, an internal standard in an inert, organic solvent is added to the container. The container is agitated and allowed to stand for a period of time sufficient to allow the catalytically-active rhodium complex to react to form a cyano-rhodium complex. The resulting mixture is subjected to GC analysis and the concentration of the organo-phosphine compounds is determined using techniques and calculation well-known to those skilled in the art. The support-phase of the chromatographic column, the flow rates, the column temperature programming rates, the type of detector, and the internal standard used will depend on the particular organo-phosphine compound or compounds and the impurities present in the sample to be analyzed. The calculations used with the internal standard method of analysis may be found in any number of textbooks pertaining to GC analyses. It will be apparent to those skilled in the art that various chromatographic conditions and techniques for calculating the concentrations of organo-phosphines and their decomposition products may be employed in conjunction with the present invention. The GC analytical procedure may employ various methods of sample injection such as direct on-column injection, split sampling in the injection-port and automatic sample injection.

The organo-phosphine compounds, i.e., tertiary or trisubstituted phosphines, present in the material analyzed according to the present invention may be selected from the vast number of organo-phosphines described in the literature, including the patents referenced hereinabove, in conjunction with hydroformylation processes. Examples of the organo-phosphine compounds include tributylphosphine, butyldiphenylphosphine, tribenzylphosphine, tricyclohexylphosphine, 2,2'-bis(diphenylphosphinomethyl)-1,1'-phenyl, and 1,2-bis(diphenylphosphinomethyl)benzene. Additional examples of tertiary phosphines are disclosed in U.S. Pat. Nos. 4,845,306, 4,742,178, 4,774,362, 4,871,878 and 4,960,949. Typical phosphine ligands may be represented by the general formula

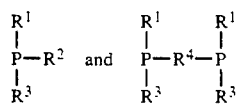

wherein $R^1$, $R^2$ and $R^3$ are the same or different and each is hydrocarbyl containing up to about 12 carbon atoms and $R^4$ is a hydrocarbylene group which links the 2 phosphorus atoms through a chain of 2 to 20 carbon atoms. Examples of the groups represented by $R^1$, $R^2$ and $R^3$ include alkyl including aryl substituted alkyl such as benzyl, cycloalkyl such as cyclohexyl, and aryl such as phenyl and phenyl substituted with one or more alkyl groups. Alkylene of 2 to 8 carbon atoms, cyclohexylene, phenylene, naphthylene and biphenylene are examples of the hydrocarbylene groups which $R^4$ may represent.

The particular cyano reagent used to convert the catalytically-active, complex form of the rhodium present in the analytical sample to a complex cyanorhodium compound, in general, is not critical. The function of the cyano reagent is to provide cyanide ion which (1) liberates the organo-phosphine ligand compounds from the rhodium atoms and (2) complexes or bonds with the rhodium atoms to "inactivate" the rhodium and thus prevent it from decomposing the phosphine compounds at the high temperatures required by the GC procedures. The rhodium residues which remain in the injector port are non-volatile and are completely passivated after the injection occurs.

It will be apparent to those skilled in the art that the cyano reagent used should (1) react with the rhodium to form the complex cyano-rhodium compound and liberate organo-phosphine ligands from the catalytically-active form of the rhodium; (2) not react with the phosphine compounds and any chromatographic internal standard present; and (3) possess sufficient solubility in solvents suitable for use in the conversion of the catalytically-active rhodium to a complex cyano-rhodium compound. The cyano reagent may be selected from inorganic cyanide salts or organic cyano-containing compounds which provide cyanide ion. Examples of the inorganic cyanides include the cyanides of the alkali and alkaline earth metals. The alkali metal cyanides such as lithium, sodium and potassium cyanides represent the preferred inorganic cyanides due to their greater solubilities in polar solvents and other considerations.

Organic cyano compounds generally are preferred because of their superior solubility in organic solvents. Examples of such compounds include cyanohydrins, aliphatic and aromatic acyl cyanides, i.e., alkanoyl and aroyl cyanides, cyanoformate esters and quaternary ammonium cyanides. Other cyano reagents which may be used, but are not preferred because of difficulties associated with handling them, include cyanogen, cyanogen halides and hydrocyanic acid.

The alkali metal cyanides, e.g., sodium and lithium cyanide; cyanohydrins, e.g., mandelonitrile, acetone cyanohydrin, lactonitrile and 2-hydroxybutyronitrile; alkyl and aralkyl cyanoformates, e.g., methyl cyanoformate, ethylcyanoformate and benzyl cyanoformate; tetra(hydrocarbyl)ammonium cyanides; and aroyl cyanides, e.g. benzoyl cyanide and the toluoyl cyanides; constitute the preferred cyano reagents. Tetra(hydrocarbyl(ammonium) cyanides wherein the total carbon content of the 4 hydrocarbyl groups is about 50 atoms, preferably about 12 to 32 atoms, are particularly preferred cyano reagents because of their solubilities in organic solvents. The hydrocarbyl groups may be selected from alkyl, cycloalkyl and aryl radicals, e.g., the groups described above for $R^1$, $R^2$ and $R^3$.

In preparing the material which is analyzed by GC in accordance with our invention, the cyano reagent is added to the sample taken from the hydroformylation process in the form of a solution in an inert, organic solvent, i.e., a liquid which will dissolve the cyano reagent and will not react with it or any of the other materials present. Examples of such solvents include alkanols such as methanol, ethanol, 2-propanol, butanol and 2-ethylhexanol; ethers such as tetrahydrofuran; esters such as butyrolactone; amd amides such as N,N-dimethylformamide, N,N-dimethylacetamide and N-methylpyrrodlidinone. If the solvent has a gas chromatographic retention time that separates it from the rentention time of compounds present in the hydroformylation mixture, the solvent may also function as an internal standard. In practice, this solution and others that are used require nitrogen purged solvents, handling under nitrogen atmosphere and bottles having crimpable, Teflon backed septa. The concentration of the cyano reagent in the solvent may be from about 0.1 to 20 weight percent, based on the total weight of the cyano reagent solution. The particular cyano reagent, solvent and concentration preferably provide a solution which is stable over an extended period of time and thus may used periodically in the analytical procedure described herein.

The amount of cyano reagent used in the preparation of the material to be analyzed should provide at least 1 and preferably 4 equivalents or moles of cyanide ion per gram-atom of rhodium present. However, the amount normally used provides from about 10 to 50 moles of cyanide ion per gram-atom of rhodium.

In accordance with known analytical procedures, the sample of material analyzed by the process of our invention also contains a chromatographic internal standard. Examples of materials which may function as the internal standard include 1,2-bis(diphenylphosphino)ethane dioxide, 1,3-bis(diphenylphosphino)propane dioxide, dodecanol, anthracene, triphenylphosphine oxide and the like. The choice of the internal standard compound will depend upon chromatographic properties of the compounds to be quantified by the analysis. Good analytical criteria for internal standards, in general, require chemical stability to the conditions of the analysis. The retention time of the eluted chromatographic peak of the internal standard should not interfere with the peaks of any of the organophosphorus compounds or other compounds present in the mixture and the retention time of the internal standard should approximate those of the organophosphorus compounds present to aid in linear peak area responses as a function of oranophosphorus compound concentrations.

The preferred internal standard compounds are tertiary phosphine oxides which are solid materials that are easily prepared in essentially pure form and are stable to long term storage. The internal standard compound may be selected from a substantial number of known tertiary phosphine oxides so that the compound is designed for a given transition metal/phosphine catalyst system on the basis of different retention times. For the very high boiling bis-phosphine compounds described in the examples presented below, the preferred internal standard compounds are 1,2-bis(diphenylphosphino)ethane dioxide (1,2-DIOXIDE) and, especially, 1,3-bis(diphenylphosphino)propane dioxide (1,3-DIOXIDE) because of its greater solubility in organic solvents. The 1,2-DIOXIDE and 1,3-DIOXIDE have retention times of 19.26 minutes and 20.62 minutes, respectively, using the chromatography conditions described in the examples. The peaks produced by 1,2-DIOXIDE and 1,3-DIOXIDE do not interfere with any of the impurities present in the catalytically-active material sampled from hydroformylation processes. The thermal stability, insensitivity to oxidation and the crystallinity of these materials for purification make them desirable for use as high temperature gas chromatography standards.

The 1,3-DIOXIDE is particularly preferred due to its superior solubility in organic solvents. The 1,2-DIOXIDE forms about a 2 weight percent saturated solution in n butanol at room temperature and is less soluble in other solvents whereas the 1,3-DIOXIDE is extremely soluble in all alcohols and other polar solvents.

The following examples describe the preparation of two bis-phosphines dioxide compounds which may be used as the internal standard of the analytical process provided by the present invention.

REFERENCE EXAMPLE 1

A 1 liter Erhlenmeyer flask was charged with 1,2-bis(diphenylphosphino)ethane (40.0 g, 0.10 mole), a Teflon-coated stir bar, glacial acetic acid (400 ml) and 20 mg of Rh(I) acetylacetonate dicarbonyl (RhAcAc) oxidation catalyst. The slurry was warmed to 40° C. and 30% aqueous hydrogen peroxide (24.9 grams, 0.22 mole $H_2O_2$) was added dropwise over 15 minutes. The heat generated required cooling to maintain a temperature of 40° C. The mixture became homogeneous about half way through the addition. The mixture was stirred at 40° C. for an additional 30 minutes and was filtered hot to remove some insoluble material. The filtrate was stripped on a rotary evaporator at 60° C. down to 0.25 torr. An off-white residue (50.23 g) of crude 1,2-bis(diphenylphosphino)ethane dioxide (1,2-DIOXIDE) crystals remained. This material was crystallized from 800 ml of a 3:1 volume ratio of isopropanol/tetrahydrofuran. The mixture was filtered hot to remove traces of turbidity and the filtrate was cooled and seeded at 50° C. induce crystallization. After cooling with stirring to room temperature, the mixture was filtered and washed with 2×100 mL of isopropanol. The product was dried under a stream of nitrogen and vacuum to yield 21.77 grams of pure 1,2-DIOXIDE.

REFERENCE EXAMPLE 2

To a 250 ml, Ehrlenmeyer flask was added 1,3-bis(diphenylphosphino)propane (4.13 grams, 10.0 mmole, Aldrich Chemical Co.), 50 mL glacial acetic acid, a magnetic stir bar and 5 mg of Rh(I)acetylacetonate dicarbonyl oxidation catalyst. Aqueous 30% hydrogen peroxide (2.84 grams, 25 mmole) was dissolved separately in 20 mL of glacial acetic acid. The bis-phosphine/acetic acid slurry was stirred while the peroxide solution was added dropwise over 20 minutes. The mixture became homogeneous during the addition. The exothermic reaction warmed the mixture up to a constant 40° C. temperature. The mixture was stirred an additional 15 minutes and the flask then was placed on a steam bath and swept with nitrogen to remove the acetic acid. A heavy yellow oil of the acetic acid complex remained. The complex was dissolved in 100 ml of methylene chloride and transferred into a separatory funnel. The mixture was extracted with 2×100 ml of a 15% aqueous sodium hydroxide solution to break the acid complex. The methylene chloride solution was then washed with 200 mL of water to remove any salts. The methylene chloride was stripped away with a nitrogen stream on the steam bath leaving behind 5.36 grams of the crude product as a heavy yellow oil. The residue was treated with 20 ml of toluene and heated to 100° C. to achieve complete solution, the solution was filtered hot to remove traces of solid and the solution then was supercooled to cause the formation of fine crystals. A stir bar was added and the mixture was warmed to 50° C. to "age" the crystals and then cooled with stirring to room temperature. The crystals were isolated by suction on Teflon filter paper, washed with 2×5 ml of toluene and dried by suction. The net weight of white crystals of 1,3-bis(diphenylphosphinepropane dioxide (1,3-DIOXIDE) melting at 136°-138° C. was 3.17 grams.

The internal standard is added to the material to be analyzed as a solution in an inert organic solvent, preferably in the same solution which contains the cyano reagent. Examples of possible solvents are set forth above relative to the description of the cyano reagent solutions. The amount of the internal standard added to the material to be analyzed typically provides a weight ratio internal standard compound to organo-phosphine compound to be analyzed of about 1:10 to 10:1, most preferably about 1:1.

Our invention is further illustrated by the following examples. The GC instrument used in our experimental studies was a Hewlett Packard Model 5890 gas chromatograph with a flame ionization detector. This work used a 7 meter×0.25 mm internal diameter DB-5 capillary column with a 0.25 micron film thickness. The chromatograph has a septum purge and operated in a split flow mode with approximately a 30/1 split ratio. The column back pressure was set at 10 psig with He carrier gas. The injector port temperature and detector temperatures were 275° and 300° C., respectively. The sample size was 0.2 microliters and was hand injected for these particular studies. The initial column temperature was 40° C. with no initial temperature hold time. The column was heated at 15° C. per minute to 300° C. as the final temperature with a hold time of 20 minutes at 300° C. In practice, before starting a series of analyses, the column is baked out at 300° C. for 15 minutes to remove accumulated septum bleed or decomposition products that slowly accumulate at the head of the column from the injector port.

The samples of catalytically-active material used in our work were obtained from a bench-scale hydroformylation reactor wherein propylene was hydroformylated at 105° C. and 260 psig in the presence of a catalyst system comprising rhodium and 2,2'-bis(diphenylphosphinomethyl)-1,1'-phenyl (BISBI). The hydroformylation mixture contained 125 mg Rh per liter and the ratio of moles BISBI:atoms Rh was 5:1. The samples of material were collected under an argon atmosphere and stored in a nitrogen box. These samples are normally allowed to degas at room temperature in an oxygen-free environment to allow the retained propylene to achieve a normal equilibrium concentration required for practical sample manipulation.

The solution of a cyano reagent and internal standard compound used in our experimental work was prepared from 1,3-DIOXIDE, tetrabutylammonium cyanide (TBACN) and n-butanol. A four-ounce, crimpable bottle was fitted with a cap and septum without being crimped. The bulk of the air is purged with nitrogen and the bottle is tared to an accuracy of 0.1 mg. The 1,3-DIOXIDE is added and the net weight is calculated. The bottle is gently purged with nitrogen (so as not to remove 1,3-DIOXIDE). The bottle is then taken to a nitrogen box where the TBACN is added and the bottle with the uncrimped cap in place is reweighed to get the net weight of TBACN. TBACN IS BOTH EXTREMELY HYGROSCOPIC AND VERY TOXIC. SPECIAL PRECAUTIONS SHOULD BE TAKEN TO AVOID SPILLAGE AND ANY KIND OF CONTACT WITH THIS MATERIAL. The bottle is then taken back to the nitrogen box again where the n-butanol solvent is added, the bottle is crimped and then weighed a final time to get the net weight of butanol added. The weight percentages of the two compounds may then be calculated. Target concentrations are 1-2 weight percent for the 1,3-DIOXIDE and 13-14 weight percent for the TBACN.

Crimpable, 2-mL sample vials, a nitrogen box and an analytical balance are used in the preparation of the samples for GC analysis. The sample vial is first labeled and then tared with the crimp cap sitting on the top of the vial. The vial is then taken to the nitrogen box where any trace of air is blown out with a stream of nitrogen. A 1 mL sample of degassed Rh/BISBI catalyst sample is syringed in and the vial is crimped. Care is taken not to spill any liquid on the outside of the vial or to get contamination in the vial. The vial is then reweighed to get the net weight of catalyst solution added. The vial is then taken back to the nitrogen box where 0.2 ml of a solution of a cyano reagent and internal standard compound is injected with a syringe having a fine and sharp needle. Care again must be taken not to squirt this reagent on the outside of the vial nor on the top of the Teflon backed septum. The vial is then reweighed to get the net weight of solution added. The mixture is then shaken well at room temperature, allowed to stand about five minutes prior to injection. The catalyst solution normally changes color from a yellow orange to pale yellow as the CN/Rh complexes are formed.

From these net weights and the concentration of the internal standard, the net weight of internal standard added is determined and the net weight of contained BISBI can be calculated using the gas chromatographic factor of BISBI with the internal standard and the chromatographic areas of the BISBI and the internal standard peaks. All the calculations are normal as is used with standard gas chromatography procedures.

$$\text{BISBI wt} = \frac{(\text{IS wt}) \times (\text{IS \%}) \times (\text{GCF}) \times (\text{BISBI area})}{(\text{IS area}) \times 100}$$

$$\text{BISBI \% in sample} = \frac{\text{BISBI wt}}{\text{Sample wt}} \times 100\%, \text{ wherein}$$

BISBI wt is the weight BISBI in mg;

IS wt is the weight of the internal standard solution added in mg;

IS % is the weight percent concentration of the internal standard in the internal standard solution;

GCF is the chromatographic response factor of BISBI with the internal standard;

BISBI area is the electronic area percent obtained from the BISBI peak during electronic peak integration;

IS area is the electronic area percent obtained from the internal standard peak during electronic peak integration;

BISBI % in sample is the weight percent BISBI in the sample analyzed; and

Sample weight is the net weight in mg of the catalyst sample added to the 2 mL vial.

The gas chromatographic factor may be determined using the internal standard solution in combination with a sample of BISBI solution of known concentration. A relatively pure sample of solid BISBI is recrystallized from isopropanol, filtered and washed with nitrogen-purged isopropanol in the nitrogen box and dried under high vacuum. A solution of this solid in nitrogen-purged tert-butylbenzene is prepared using the analytical balance and a crimp seal bottle to obtain a solution of known BISBI concentration. Algebraic manipulation of the above formula can solve for the GCF when used with gas chromatographic area percentages of BISBI and the internal standard in combination with known weights of BISBI and the internal standard used to prepare the sample.

EXAMPLE 1

A sample of hydroformylation mixture having a net weight of 927.1 mg was injected with 168.7 mg of a butanol solution containing 4.442 weight percent 1,3-bis(pdiphenylphosphino)propane dioxide (1,3-DIOXIDE) and 13.557 weight percent tetrabutylammonium cyanide (TBACN) The area percent of the peaks were:

| | |
|---|---|
| 1,3-DIOXIDE | 0.5537 |
| BISBI | 0.1570 |
| BISBI Monoxide | 0.0788 |

The gas chromatographic factor was 0.8556. The BISBI concentration of a sample of hydroformylation mixture was determined using the above formulas. By carrying out the above calculations, the concentration of BISBI in the hydroformylation mixture was determined to be 0.196 weight percent. By using analogous calculations, the concentration of BISBI Monoxide was determined to be 0.107 weight percent. The calculation for the weight of BISBI in mgs in the sample was:

$$\frac{(168.7\text{ mg}) \times (4.442\%) \times (0.8556) \times (0.1570\%)}{(0.5537\%) \times (100\%)} = 1.818 \text{ mg}$$

$$\text{BISBI \%} = \frac{1.818 \text{ mg}}{927.1 \text{ mg}} \times 100 = 0.196\%$$

The normalized area percent for each peak produced by BISBI, BISBI monoxide and BISBI decomposition products and the time (Time, minutes) at which each such component is eluted, i.e., the peak retention time, are given below.

| Time | Normalized Area Percent |
|---|---|
| 14.37 | 1.69 |
| 17.86 | 1.84 |
| 22.13 | 64.24 |
| 26.83 | 32.24 |

The compound eluting at 14.37 minutes is 1-diphenyl-phosphinomethyl-2'-methyl-1,1'-phenyl, a compound produced by the decomposition of BISBI in the hydroformylation process and/or present as an impurity in the BISBI used in the hydroformylation process. BISBI elutes at 22.13 minutes and BISBI monoxide elutes at 26.83 minutes.

The normalized area percentages are associated with BISBI, BISBI oxides and BISBI decomposition products. The normalized area percent for a given BISBI decomposition product "X" is:

$$\frac{\text{Normalized}}{\text{Area \% for } X} = \frac{(\text{Area } X)(100)}{\Sigma \text{ Areas of BISBI, BISBI Oxides and BISBI Decomposition Products}}$$

COMPARATIVE EXAMPLES 1 AND 2

To demonstrate the detrimental effect which rhodium exhibits on the accuracy of GC analysis for BISBI, two BISBI solutions were prepared and analyzed by GLC according to the procedure described above. The first solution (Comparative Example 1, C-1) consisted of 16.95 mg BISBI in 282.5 mg of 2 ethylhexanal and 2945.8 mg butanol. The second solution (Comparative Example 2, C-2) was identical to the first solution except that it included 1.9 mg Rh(I)acetylacetonate dicarbonyl, giving a BISBI:Rh mole ratio of 4.18:1. This rhodium compound reacts with BISBI to form a Rh/BISBI complex. The normalized area percent for each peak produced by BISBI and any BISBI monoxide or BISBI decomposition products present and the time (Time, minutes) at which each such component is eluted, i.e., the peak retention time, are given in Table I. The analytical results for Comparative Example 2 show the decomposing effect which rhodium has on BISBI. The compounds eluting at 10.73 and 12.53 minutes have not been identified.

EXAMPLE 2

To demonstrate the advantageous effect of including a cyano reagent in analysis of solutions containing BISBI and rhodium, 166.9 mg 13.56 weight percent solution of tetrabutylammonium cyanide (TBACN) in n-butanol was added to 768.0 mg of the solution of Comparative Example 2. This amount of TBACN provided a TBACN:Rh mole ratio of 45.8:1. The normalized area percent for each peak produced by BISBI and 1-diphenylphosphinomethyl-2'-methyl-1,1'-phenyl and the time (Time, minutes) at which each such component is eluted are given in Table I. The analytical results for Example 2 show that the cyano reagent TBACN has completely inactivated the decomposing effect which rhodium has on BISBI.

TABLE I

| Time | | Normalized Area Percent | | |
|---|---|---|---|---|
| | | Example C-1 | Example C-2 | Example 2 |
| 10.73 | | 0.0 | 12.51 | 0.0 |
| 11.54 | | 0.0 | 0.0 | 0.0 |
| 11.91 | | 0.0 | 0.0 | 0.0 |
| 12.53 | | 0.0 | 3.67 | 0.0 |
| 14.37 | | 2.56 | 5.88 | 2.64 |
| 15.71 | | 0.0 | 0.0 | 0.0 |
| 17.86 | | 0.0 | 0.0 | 0.0 |
| 22.13 | (BISBI) | 97.44 | 77.94 | 97.36 |
| 26.83 | | 0.0 | 0.0 | 0.0 |

EXAMPLES 3–5 AND COMPARATIVE EXAMPLE 3

The effectiveness of mandelonitrile, benzyl cyanoformate and benzoyl cyanide was investigated using a sample of a catalytically-active solution of a BISBI/rhodium complex obtained from a bench-scale hydroformylation production system wherein the BISBI:Rh mole ratio was approximately 5:1. The analytical samples were prepared by mixing 950 mg samples of the hydroformylation mixture with 1.62 mg mandelonitrile (Example 3); 1.96 mg benzyl cyanoformate (Example 4); and 1.59 mg benzoyl cyanide (Example 5). The amount of each cyano reagent used provided a cyano reagent:Rh mole ratio of approximately 10:1. After the addition of the cyano reagent, the analytical samples were warmed with agitation to 50° C. for 20 minutes. The analytical samples thus prepared, and a sample of the hydroformylation solution which was not treated with any cyano reagent (Comparative Example 3), were analyzed by te GC procedure described hereinabove. The normalized area percent for each peak produced by BISBI, BISBI monoxide, 1-diphenylphosphinomethyl-2'-methyl-1,1'-biphenyl and other BISBI decomposition products and the time (Time, minutes) at which each such component is eluted are given in Table II. The Table II data show that the percentage BISBI in the samples is substantially higher in the samples that were treated with one of the cyano reagents. The three cyano reagents result in a substantial reduction in the area percentages of peaks associated with BISBI decomposition products.

TABLE II

| Time | | Normalized Area Percent | | | |
|---|---|---|---|---|---|
| | | Example C-3 | Example 3 | Example 4 | Example 5 |
| 10.73 | | 14.52 | 1.89 | 3.12 | 2.65 |
| 12.55 | | 4.78 | 0.0 | 0.99 | 0.0 |
| 14.37 | | 4.56 | 1.55 | 1.75 | 1.63 |
| 15.71 | | 3.20 | 1.03 | 1.41 | 1.36 |
| 16.73 | | 1.80 | 2.50 | 2.47 | 2.53 |
| 22.13 | (BISBI) | 39.56 | 58.01 | 55.02 | 56.23 |
| 26.83 | | 31.59 | 35.02 | 35.25 | 35.61 |

As mentioned hereinabove, 14.37 minutes is 1-diphenylphosphinomethyl-2'-methyl-1,1'-phenyl, BISBI and BISBI monoxide elute at 14.37 minutes, 22.13 minutes and 26.83 minutes, respectively.

EXAMPLES 6 AND 7

The effect of increasing the mandelonitrile:Rh mole ratio was investigated using the procedure of Example 3 modified by the addition of 8.09 mg (Example 6) and 16.2 mg (Example 7) of mandelonitrile. The analytical samples thus prepared were analyzed by the GC procedure described hereinabove. The normalized area percent for each peak produced by BISBI, BISBI monoxide, 1-diphenylphosphinomethyl-2'-methyl-1,1'-phenyl and other BISBI decomposition products and the time (Time, minutes) at which each such component is eluted are given in Table III along with the data for Example 3 which is also shown in Table II. The Table III data show that increasing the mandelonitrile:Rh mole ration above 10:1 does not change significantly the effect of the mandelonitrile cyano reagent.

TABLE III

| | Normalized Area Percent | | |
|---|---|---|---|
| Time | Example 3 | Example 6 | Example 7 |
| 10.73 | 1.89 | 1.53 | 1.20 |
| 12.55 | 0.0 | 0.0 | 0.0 |
| 14.37 | 1.55 | 1.67 | 1.71 |
| 15.71 | 1.03 | 1.13 | 1.07 |
| 16.73 | 2.50 | 2.60 | 2.52 |
| 22.13 | 58.01 | 51.33 | 55.15 |
| 26.83 | 35.02 | 41.74 | 38.35 |

EXAMPLES 8-10 AND COMPARATIVE EXAMPLE 4

The effectiveness of lithium cyanide at LiCN:RH mole ratios of 10:1, 50:1 and 100:1 was investigated using a sample of the catalytically-active solution of a BISBI/rhodium complex used in Example 1. The analytical samples were prepared by mixing 950 mg of the hydroformylation mixture with 22.7 mg (Example 8, LiCN:Rh=10:1), 11.5.4 mg (Example 9, LiCN:Rh=50:1)) and 229.9 mg (Example 10, LiCN:Rh=100:1) of a 1.74 weight percent solution of lithium cyanide in N,N-dimethylformamide. After the addition of the lithium cyanide, the analytical samples were warmed with agitation to 50° C. for 20 minutes. The analytical samples thus prepared, and a sample of the hydroformylation solution which was not treated with any cyano reagent (Comparative Example 4), were analyzed by the GC procedure described hereinabove. The normalized area percent for each peak produced by BISBI, BISBI monoxide, 1-diphenylphosphinomethyl-2'-methyl-1,1'-phenyl and other BISBI deoomposition products and the time (Time, minutes) at which each such component is eluted are given in Table IV.

TABLE IV

| | Normalized Area Percent | | | |
|---|---|---|---|---|
| Time | Example C-4 | Example 8 | Example 9 | Example 10 |
| 10.73 | 16.64 | 4.55 | 5.38 | 3.53 |
| 12.55 | 5.98 | 1.28 | 0.0 | 0.0 |
| 14.37 | 5.08 | 1.52 | 0.39 | 0.85 |
| 15.71 | 3.37 | 1.22 | 0.34 | 0.06 |
| 16.77 | 1.78 | 0.0 | 0.0 | 0.0 |
| 22.51 | 34.51 | 50.97 | 52.38 | 48.11 |
| 26.83 | 32.64 | 40.47 | 39.94 | 47.51 |

TABLE IV-continued

The Table IV data show that superior results are achieved by the use of high LiCN:Rh ratios. Although potassium cyanide also is an effective cyano reagent, its low solubility in organic solvents, e.g., maximum solubility in methanol of about 4 weight percent at room temperature, limits its use in organic media.

EXAMPLES 11-13

Using a sample of the catalytically-active solution of a BISBI/rhodium complex used in Example 1, an analytical sample was prepared by mixing 927.1 mg of the hydroformylation mixture with 168.7 mg of a 13.56 weight percent solution of TBACN in butanol. After the addition of the TBACN, the analytical samples were analyzed by the GC procedure described hereinabove after standing for (i) 1.5 minutes (Example II), (ii) 56 minutes (Example 12), and 100 minutes (Example 13). The normalized area percent for each peak produced by BISBI, BISBI Monoxide, 1 diphenylphosphinomethyl 2'-methyl1,1'-phenyl and other BISBI decomposition products and the time (Time, minutes) at which each such component is eluted are given in Table V.

TABLE V

| | | Normalized Area Percent | | |
|---|---|---|---|---|
| Time | | Example 11 | Example 12 | Example 13 |
| 10.73 | | 1.41 | 1.62 | 1.33 |
| 12.55 | | 0.0 | 0.0 | 0.0 |
| 14.37 | | 1.65 | 1.78 | 1.85 |
| 15.71 | | 0.0 | 1.07 | 1.04 |
| 17.86 | | 1.93 | 2.04 | 2.05 |
| 22.13 | (BISBI) | 63.26 | 59.47 | 59.58 |
| 26.83 | (BISBI monoxide) | 31.75 | 34.01 | 34.15 |

The Table V data show that the TBACN cyano reagent reacts quickly with the BISBI/rhodium complex and that long contact times prior to analyses does not change materially the analytical values. The increase of BISBI monoxide is due to contamination with trace amounts of air resulting from multiple syringe sampling of the vial.

EXAMPLE 14 AND COMPARATIVE EXAMPLE 5

A sample of a catalytically-active solution of a complex of 1,2-bis(diphosphinomethyl)benzene (OXYL) and rhodium was obtained from a bench-scale propylene hydroformylation production system wherein the OXYL:Rh mole ratio was approximately 5:1. A 928.6 mg portion of the hydroformylation solution was mixed at room temperature with 153.6 mg of a butanol solution containing 4.442 weight percent 1,3-DIOXIDE and 13.557 weight percent TBACN, giving a TBACN:Rh mole ratio of 46:1. The analytical sample thus prepared was allowed to stand at room temperature for 20 minutes, and a sample of the hydroformylation solution which was not treated with any cyano reagent (Comparative Example 5), were analyzed by the GC procedure described hereinabove. The normalized area percent for each peak produced by OXYL, OXYL, Dioxide and OXYL decomposition products and the time (Time, minutes) at which each such component is eluted are given in Table VI. The Table VI data show that the percentage OXYL is substantially higher in the samples that wee treated with TBACN.

TABLE VI

| Time | Normalized Area Percent | |
|---|---|---|
| | Example C-5 | Example 14 |
| 8.37 | 3.77 | 0.0 |
| 10.47 | 4.47 | 0.0 |
| 10.64 | 8.89 | 0.0 |
| 11.83 | 9.33 | 1.94 |
| 12.91 | 14.71 | 1.34 |
| 14.13 | 0.79 | 0.0 |
| 18.37 (OXYL) | 52.46 | 86.26 |
| 27.26 | 5.69 | 10.45 |

The compound eluting at 18.37 minutes is OXYL and the compound eluting at 27.26 minutes is OXYL Dioxide. The unnormalized peak areas were 0.2443% for the OXYL and 0.6347 for the 1,3-DIOXIDE and the GCF value was determined to be 0.808. Using the formulas and calculations employed in Example 1, the concentration of OXYL in the hydroformylation solution was determined to be 0.283 weight percent.

The invention has been described in detail with particular reference to preferred embodiments thereof, but it will be understood that variations and modifications may be effected within the spirit and scope of the invention.

We claim:

1. Process for determining the concentration of organo-phosphine compounds present in a solution containing a complex of an organo-phosphine compound and rhodium which comprises the steps of:
   (a) contacting the solution with a cyano reagent to convert the organo-phosphine:rhodium complex to a cyano-rhodium complex; and
   (b) subjecting the solution obtained from step (a) to gas-liquid chromatography analysis.

2. Process according to claim 1 for determining the concentration of organo-phosphine compounds present in a solution containing a complex of an organo-phosphine compound and rhodium which comprises the steps of:
   (a) contacting the solution with a cyano reagent to convert the organo-phosphine:rhodium complex to a cyano-rhodium complex wherein:
      the cyano reagent is selected from the group consisting of alkali metal cyanides, cyanohydrins, cyanoformate esters, tetra(hydrocarbyl)ammonium cyanides and aroyl cyanides; and the amount of cyano reagent used provides at least 4 moles cyanide ion per gram-atom rhodium; and
   (b) subjecting the solution obtained from step (a) to gas chromatography analysis.

3. Process according to claim 2 wherein the organo-phosphine compounds are selected from the group consisting of mono- and bis-phosphine compounds having the respective general formulae:

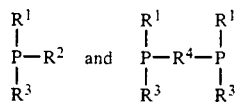

wherein $R^1$, $R^2$ and $R^3$ are the same or different and each is hydrocarbyl containing up to about 12 carbon atoms and $R^4$ is a hydrocarbylene group which links the 2 phosphorus atoms through a chain of 2 to 20 carbon atoms, oxides, of said mono- and bis-phosphine compounds, decomposition products of said mono and bis-phosphines, and mixtures thereof.

4. Process according to claim 1 for determining the concentration of organo-phosphine compounds present in a solution containing a complex of an organo-phosphine compound and rhodium which comprises the steps of:
   (a) contacting the solution with a cyano reagent to convert the organo-phosphine:rhodium complex to a cyano-rhodium complex wherein:
      the cyano reagent is selected from the group consisting of tetra(hydrocarbyl)ammonium cyanides wherein the: total carbon content of the 4 hydrocarbyl groups is about 12 to 32 atoms; and
      the amount of cyano reagent used provides about 10 to 50 moles cyanide ion per gram-atom rhodium; and
   (b) subjecting the solution obtained from step (a) to gas chromatography analysis.

5. Process for determining the concentration of organo-phosphine compounds present in a solution containing a complex of an organo-phosphine compound and rhodium which comprises the steps of:
   (a) contacting the solution with a second solution comprising a cyano reagent, a gas chromatographic internal standard and an inert solvent to convert the organo-phosphine:rhodium complex to a cyano rhodium complex; and
   (b) subjecting the solution obtained from step (a) to gas chromatography analysis.

6. Process according to claim 5 wherein (a) the cyano reagent is selected from the group consisting of alkali metal cyanides, cyanohydrins, cyanoformate esters, tetra(hydrocarbyl)ammonium cyanides and aroyl cyanides and (b) the amount of cyano reagent used provides at least 4 moles cyanide ion per gram-atom rhodium.

7. Process according to claim 5 wherein (a) the cyano reagent is a tetra(hydrocarbyl)ammonium wherein the total carbon content of the 4 hydrocarbyl groups is about 12 to 32 atoms and (b) the amount of cyano reagent used provides about 10 to 50 moles cyanide ion per gram-atom rhodium.

8. Process for determining the concentration of organo-phosphine compounds present in a solution collected from a hydroformylation production system and containing a complex of an organo-phosphine compound and rhodium which comprises the steps of:
   (a) contacting the solution with a second solution comprising a tetra(hydrocarbyl(ammonium wherein the total carbon content of the 4 hydrocarbyl groups is about 4 to 32 atoms, a chromatographic internal standard and an inert, an organic solvent to convert the organo-phosphine:rhodium complex to a cyanorhodium complex wherein the amount of cyano reagent used provides about 10 to 50 moles cyanide ion per gram-atom rhodium; and
   (b) subjecting the solution obtained from step (a) to gas chromatography analysis.

* * * * *